United States Patent [19]

Gindler

[11] 4,337,064
[45] Jun. 29, 1982

[54] ALBUMIN DETERMINATION METHOD

[75] Inventor: E. Melvin Gindler, Union City, Calif.

[73] Assignee: Sherwood Medical Industries Inc., St. Louis, Mo.

[21] Appl. No.: 189,777

[22] Filed: Sep. 22, 1980

Related U.S. Application Data

[63] Continuation-in-part of Ser. No. 106,028, Dec. 21, 1979, abandoned, which is a continuation of Ser. No. 895,084, Apr. 10, 1978, abandoned, which is a continuation of Ser. No. 693,866, Jun. 8, 1976, abandoned.

[51] Int. Cl.³ .................. G01N 33/48; C09K 3/00
[52] U.S. Cl. ........................... 23/230 B; 23/902; 252/408
[58] Field of Search ............... 252/408; 23/230 B, 902

[56] References Cited

U.S. PATENT DOCUMENTS

| | | | |
|---|---|---|---|
| 2,986,453 | 5/1961 | Collins | 23/230 B |
| 3,533,749 | 10/1970 | Kleihman | 23/230 B |
| 3,558,278 | 1/1971 | Louderback et al. | 23/230 B |
| 3,754,864 | 8/1973 | Gindler | 23/230 B |
| 3,754,865 | 8/1973 | Gindler | 23/230 B |
| 3,853,465 | 12/1974 | Rush et al. | 23/230 B |
| 3,873,272 | 3/1975 | Wakefield et al. | 23/230 B |
| 3,884,637 | 5/1975 | Gindler | 23/230 B |
| 3,915,643 | 10/1975 | Gindler | 23/230 B |
| 3,953,359 | 4/1976 | Gindler | 252/408 |
| 4,219,337 | 8/1980 | Grossberg et al. | 252/408 |

OTHER PUBLICATIONS

Doumas, B. T. et al., Clin. Chem. Acta., vol. 31, pp. 87–96, (1971).
Miyada, D. et al., Clin. Chem., vol. 18, No. 1, pp. 52–56, (1972).

*Primary Examiner*—Teddy S. Gron
*Attorney, Agent, or Firm*—Wegner, McCord, Wood & Dalton

[57] ABSTRACT

A quantitative colorimetric or spectrophotometric method of determining analyte albumin using a specie specific dye-based color reagent is disclosed. The method utilizes a standard solution comprising an aqueous solution of albumin of different specie than that of the analyte and a water soluble surfactant containing at least one hydrophobic group of contiguous carbon atoms. The surfactant is of a type and present in an amount such that the standard solution mimics, with respect to spectrophotometric response, an aqueous solution of the analyte when the standard solution and the analyte solution contain the same concentrations of albumin and color reagent.

9 Claims, No Drawings

ALBUMIN DETERMINATION METHOD

CROSS-REFERENCE TO RELATED APPLICATIONS

This application is a continuation-in-part of Ser. No. 106,028 filed Dec. 21, 1979 and now abandoned, which is a continuation of Ser. No. 895,084 filed Apr. 10, 1978 and now abandoned, which is a continuation of Ser. No. 693,866 filed June 8, 1976 and now abandoned.

BACKGROUND OF THE INVENTION

1. Field of the Invention

This invention relates to an analysis of biologic fluids and, more particularly, this invention relates to the spectrophotometric analysis of albumin in biologic fluids using dye binding methods wherein the color imparting dye exhibits species specificity.

2. Description of the Prior Art

Spectrophotometric methods are widely used for determining the concentration of various constituents in biologic fluids such as blood. The methods usually involve adding a color-forming reagent, generally in aqueous solution, to the fluid to form a colored complex with the analyte to be detected.

The complex has a characteristic wavelength of maximum light absorption. By exposing a sample of the fluid containing the complexed reagent to a light source of the wavelength of maximum absorption (or the wavelength of maximum difference of absorption with respect to the reagent in a blank), and thereafter measuring the degree of light absorption, the concentration of the analyte in the biologic fluid can be determined with reference to a calibration graph constructed from absorption measurements made on calibrator solutions comprising standard solutions containing the reagent and known analyte concentrations.

The absorbance of both the sample and the standard are generally read against a blank containing the reagent solution. Of course, to accomplish the determination, a color-forming reagent must be selected which has the ability to form a colored derivative with the analyte, which derivative differs from the reagent in either intensity or absorption wavelength characteristics.

With respect to the determination of albumin in sera, several general types of dyes are useful as components of color-forming reagents. These include the sulphonphthalein dyes such as bromcresol green, hydroxyphenyl azo dyes such as 2-(hydroxyphenylazo)-benzoic acid (commonly called HABA), and biuret type reagents.

A dye marketed by Pierce Chemical Company of Rockford, Ill. (now Lancer Division, Sherwood Medical Industries Inc.) under the mark "Spectru AB2" is quite useful. A particularly advantageous albumin determination procedure employing sulphonphthalein dyes is described in Gindler U.S. Pat. No. 3,884,637 issued May 20, 1975. HABA and SpecTru AB2 TM dyes have been used for determination of albumin for a number of years. Procedures using biuret are most useful when total protein (albumin plus globulin) is to be determined, since biuret forms colored complexes with both of these proteins. When biuret is to be used for albumin determination alone, it is necessary to first remove globulin from the sample.

There are many instances when it is desirable to determine globulin in addition to albumin concentration. These determinations are frequently accomplished by determining albumin with an albumin-binding color reagent and then using biuret reagent to determine the total protein concentrations. By difference, the globulin concentration can then be ascertained.

Some albumin-binding dyes exhibit species specificity with respect to albumin. Thus, whereas bromcresol green and biuret reagents display little difference in their binding capacities with respect to either human or bovine albumin, SpecTru AB2 TM dye exhibits a more pronounced capacity to bind human albumin than bovine albumin.

As a result, when albumin concentration is to be determined in human sera using such a dye, it has heretofore been necessary to also use human albumin in the standard. However, the availability of pure human albumin has become irregular, in part because sources have sometimes provided human albumin potentially carrying hepatitis. On the other hand, suitable bovine albumin is generally available in good supply.

SUMMARY OF THE INVENTION

Accordingly, a principal object of the invention resides in providing a method of albumin determination using a standard solution of one specie of albumin which can be used in connection with the spectrophotometric determination of another specie of albumin utilizing a species specific dye.

A further object of the invention is to provide a standard solution having the characteristics recited in the principal object which can be used as the standard for both the determination of albumin and the determination of total protein.

Briefly stated, the present invention is based on the discovery that the spectrophotometric response of an aqueous solution of one species of albumin and a species specific dye-based color reagent can, by addition thereto of a particular type of surfactant, be made to closely mimic the spectrophotometric response of an aqueous solution containing the same concentrations of the dye-based color reagent and another specie of albumin. As a result, for example, an aqueous solution containing the surfactant, an azo dye color reagent and bovine albumin has been found to be useful as a standard in the spectrophotometric procedure for determining human albumin concentration.

Other objects and advantages of the invention will be apparent from the following detailed description.

DETAILED DESCRIPTION OF THE INVENTION

In its broadest aspects, the present invention is useful in connection with the determination of albumin wherein the reagent dye employed exhibits species specificity with respect to albumin and wherein it is desired to use a different specie of albumin in the standard solution than that present in the analyte.

Whether the dye selected has species specificity can be readily determined by obtaining pure samples of the analyte and standard albumin, preparing aqueous solutions of the two at identical albumin concentrations, adding identical color-forming reagent compositions to both solutions and then measuring absorbance of each solution at the optimum wavelength. If the measured absorptivities of the different species at the same wavelength differ, or if the maximum absorbance is obtained at different wavelengths, then the dye exhibits the requisite species specificity.

Once it is ascertained that the dye to be used exhibits species specificity, utilization of the present invention is appropriate. To that end, a plurality of solutions are prepared containing identical sample concentrations of the standard albumin and color-forming reagent. Thereafter, a surfactant such as described below is selected and varying concentrations of the surfactant are added to the standard solutions, followed by absorbance measurements. That concentration which results in an absorbance spectrum substantially identical to that of the analyte solutions is the appropriate concentration, for the selected surfactant and dye, necessary to obtain the desired mimicing effect.

Surfactants useful according to the present invention as additives to an albumin standard solution are characterized as being water soluble and containing at least one hydrophobic group of contiguous carbon atoms. The hydrophobic group contains a chain of at least about six, and preferably at least about nine, contiguous carbon atoms. While the chain is preferably a hydrocarbon, it can contain a variety of substituents such as, for example, alkyl, aryl, halogen, etc.

The chain length of the hydrophobic group can extend up to about 20 to 25 carbon atoms. In order to be water soluble and otherwise useful, and depending on the contiguous carbon atom chain length, the surfactants also contain hydrophilic groups. In general, the selection of the hydrophilic group must be such that the surfactant is water soluble, or water solubilizable, at a solution pH of less than about 7, since acid pHs are widely used in albumin determination.

The hydrophilic group may comprise nonionic, anionic or cationic hydrophilic groups. However, with respect to cationic groups, such as provided by a quaternary nitrogen atom, it is necessary that the surfactant also contain either a nonionic hydrophilic group or an anionic group such as provided by a carboxylate or sulphonic acid part.

Further, if the surfactant's hydrophilic group is nonionic or combined cationic and nonionic, the nonionic part is preferably provided by one or more polyethylene oxide chains having at least about six, and preferably at least about nine, repeating ethylene oxide units. As a practical matter, the number of repeating units generally will not extend much above about 25. Sulphates, phosphates and sulfonates are preferred anionic hydrophilic groups.

Nonionic and cationic surfactants are generally preferred when the dye employed provides greater absorbance per gram albumin per liter with the specie of albumin in the analyte than with the specie of albumin selected for the standard. Thus, these surfactants are preferred when the analyte is human albumin, the standard is bovine albumin, and the dye employed is SpecTru AB2 TM dye. On the other hand, an anionic surfactant is most useful when the selected dye gives greater absorbance per gram albumin per liter with the albumin in the standard than with the albumin in the analyte.

The following are examples of useful additive surfactants.

A long chain betaine marketed by E. I. DuPont de Nemours & Co. under the designation "DDN" and having the structure:

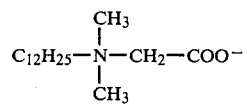

"Ethoquad ® 18/25" which is an ethoxylated, hydrocarbon cationic surfactant having the structure:

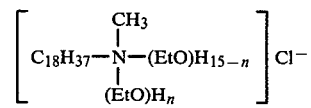

"BRIJ ® 35" which is a polyethylene oxide adduct of lauryl alcohol having the structure:

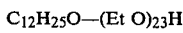

"BION ® NE-9" which is a polyethylene oxide adduct of p-nonyl phenol having the structure:

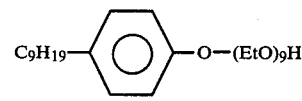

Sodium dodecylsulfate having the structure:

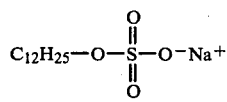

EXAMPLE

The following example illustrates the practice of the present invention:

A preservative solution is prepared containing the following ingredients in four liters of deionized water.
8.0 gm sodium azide
25 gm potassium bromide
16 gm sodium fluoride
43.45 gm phenoxy ethanol
20 gm sodium propionate
2 gm benzoic acid
2 gm disodium salt of ethylenediaminetetraacetic acid dihydrate About ½ liter of the preservative solution is placed in a one liter flask and 108 grams of bovine albumin are added thereto. 83.3 ml of DuPont product "DDN" (25% active ingredient) is added to the flask and deionized water is added to bring the volume of the modified bovine albumin solution to one liter.

A color reagent solution is then prepared containing SpecTru AB2 TM dye. The solution contains about 41.5 grams of dye in 850 liters of deionized water containing the following ingredients:
33.3 gm monoethanol amine
33.3 liter isopropanol
83.2 sodium sulphite (anhydrous)
2346 gm potassium phsophate monobasic (anhydrous)
1878 gm sodium phosphate dibasic heptahydrate
2620 ml formaldehyde (37% solution)
260 gm BION ® NE-9 ®

A concentrated biuret color reagent solution is prepared in one liter of deionized water by dissolving the following reagents therein:

16 gm cupric sulphate pentahydrate
53 gm sodium potassium tartrate tetrahydrate (Rochelle salt)
5 gm potassium iodide
85 gm sodium hydroxide A dilute biuret solution is similarly prepared in four liters of water.

A calibration graph is constructed by making appropriate dilutions of the modified bovine albumin solution which acts as a 108 gram/liter solution of albumin towards either the biuret reagent or the SpecTru AB2 TM solution. As a result, by simple dilution of portions of the modified bovine albumin solution, an appropriate calibration graph is constructed.

In making measurements on the calibrator solutions, 0.05 ml aliquots of the modified bovine albumin solutions are added to individual test tubes (13×100 mm) and 3.0 ml of the color reagent solution is added. With respect to SpecTru AB2 TM, colorimetric or spectrophotometric measurements are made at 505 nm against a reagent blank set at 0. The blank is prepared by placing 0.05 ml of distilled water and 3.0 ml of the color reagent solution in a similar type of test tube. With respect to dilute biuret reagent, the procedure is the same except that the colorimeter or spectrophotometer is set at 550 nm.

Once the calibration graph is constructed, albumin concentration and total protein concentration are readily determined. To accomplish this, 0.05 ml of human serum sample is placed in a test tube (13×100 mm) and 3.0 ml SpecTru AB2 TM reagent solution is added thereto with mixing. The color reaction occurs substantially instantaneously and, accordingly, the solution color may be read immediately after mixing against a reagent blank prepared as described above. The final solution color is stable for at least about 6 hours. The albumin concentration in the human sample can be readily obtained from the calibration graph.

To determine total protein, either a new human serum sample or the sample used for albumin determination can be employed. If the latter procedure is used, the biuret reagent solution should be added within two hours after the addition of the SpecTru AB2 TM dye solution. In determining total protein, whether in the unknown sample or for calibration purposes, 1.00 ml of the concentrated biuret reagent solution is added to 0.05 ml of the sample. The solution is then allowed to stand for about 30 minutes at room temperature during which time a characteristic lavender color develops. As mentioned above, absorbance is read at 550 nm and total protein in the sample can, as with albumin, be obtained from the calibration graph.

While the present invention has been described in connection with certain specific embodiments, it is to be understood that it is not to be limited to those embodiments. On the contrary, it is intended to cover all alternatives and modifications falling within the spirit and scope of the invention as set forth in the appended claims.

I claim:

1. In a method for the colorimetric or spectrophotometric determination of analyte albumin concentration in a fluid using an albumin specie specific dye-based color reagent, said method comprising the steps of:

(a) adding said color reagent to said fluid whereby a colored complex is formed with the analyte albumin;
   (b) exposing said fluid to a light source; and
   (c) measuring the degree of light absorption and determining the concentration of analyte albumin in said fluid by comparison of said measured degree of light absorption with the measured degree of light absorption obtained from at least one similarly treated standard solution containing a known concentration of albumin, the improvement wherein:
   said standard solution comprises an aqueous solution of known concentration of albumin of different specie than the analyte and a water soluble surfactant containing at least one hydrophobic group containing at least about nine contiguous carbon atoms and also containing a hydrophilic group, said surfactant being present in an amount such that said standard solution mimics, with respect to spectrophotometric response, an aqueous solution of the analyte albumin when said standard solution and said analyte solution contain the same concentration of albumin and color reagent and said analyte solution is free of said surfactant in said amount.

2. The method of claim 1 wherein the hydrophilic group is an anionic group selected from sulfate, phosphate or sulfonate.

3. The method of claim 1 wherein the hydrophilic group is a mixed cationic/anionic or cationic/nonionic group.

4. The method of claim 3 wherein the nonionic group is a polyethylene oxide chain having at least about nine repeating ethylene oxide units.

5. The method of claim 1 wherein the hydrophilic group is a nonionic group.

6. The method of claim 5 wherein the nonionic group is a polyethylene oxide chain having at least about nine repeating ethylene oxide units.

7. The method of claim 1 wherein the surfactant is selected from a long chain betaine; an ethoxylated, hydrocarbon cationic surfactant; a polyethylene oxide adduct of lauryl alcohol or p-nonylphenol; or sodium dodecylsulfate.

8. The method of claim 1 wherein the albumin of the standard solution is bovine, the analyte albumin is human and said surfactant is selected from

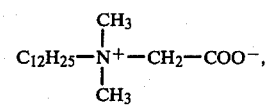

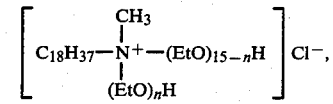

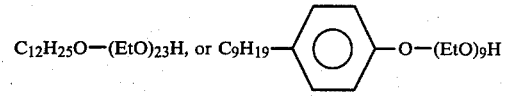

9. The method of claim 8 wherein the surfactant is

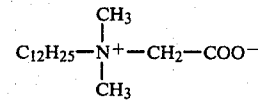

* * * * *